United States Patent [19]

Ferlazzo et al.

[11] 3,956,376

[45] May 11, 1976

[54] PROCESS FOR THE PRODUCTION OF ACROLEIN AND ACRYLIC ACID

[75] Inventors: Natale Ferlazzo, Milan; Gian Fausto Buzzi, Arona; Marcello Ghirga, Bresso, all of Italy

[73] Assignee: Societa Italiana Resine S.p.A., Milan, Italy

[22] Filed: Nov. 29, 1973

[21] Appl. No.: 420,344

[30] Foreign Application Priority Data

Nov. 30, 1972 Italy .................................. 32281/72

[52] U.S. Cl. ...................... 260/530 N; 260/533 N; 260/604 R
[51] Int. Cl.$^2$ .................... C07C 47/22; C07C 51/26
[58] Field of Search ......... 260/533 N, 530 N, 604 R

[56] References Cited
UNITED STATES PATENTS 3,755,458   8/1973   Vibaski et al. .................. 260/604 A
3,819,685   6/1974   Grasselli ........................ 260/530 N Primary Examiner—James A. Patten
Attorney, Agent, or Firm—Sughrue, Rothwell, Mion, Zinn & Macpeak

[57] ABSTRACT

An improved process for the production of acrolein from propylene and of acrylic acid from propylene or acrolein or mixtures of propylene and acrolein which essentially comprises catalytic oxidation of propylene and/or acrolein with oxygen or a gas containing molecular oxygen in the presence of an oxidation catalyst and of methanol in a quantity of from 0.01 to 1% by volume with respect to the total gaseous mixture of the reactants. Acrolein and acrylic acid are formed in the process at high conversion rates and selectivities.

8 Claims, No Drawings

PROCESS FOR THE PRODUCTION OF ACROLEIN AND ACRYLIC ACID

The present invention relates to an improved process for the production of acrolein and acrylic acid.

It is already known in the art that acrolein can be produced by catalytic oxidation of propylene in the gaseous phase with oxygen or a gas containing molecular oxygen.

It is also known that acrylic acid can be prepared catalytically in the vapour phase from propylene by first oxidizing the propylene to acrolein, separating the acrolein produced, and then oxidizing the acrolein to acrylic acid.

It is also known that acrylic acid can be prepared in the vapour phase by direct catalytic oxidation of propylene and recycling of the acrolein formed as a by-product to the oxidation reactor.

In this last case the mixture subjected to oxidation therefore consists of propylene and acrolein.

Various combinations of cobalt, molybdenum, arsenic, tin, tellurium, manganese, nickel, bismuth, phosphorus, boron, iron, vanadium, rhenium, tungsten, zinc, or antimony, either as oxides or as compounds consisting of at least two of the metals mentioned and oxygen, are normally used as catalysts for the oxidations described.

However, these processes are characterized in that the conversion of the reactants is never complete and that by-products are also formed in appreciable quantities, particularly total oxidation products such as water and carbon dioxide.

This naturally leads to rather low conversions of the reactants and selectivities for the desired products, which vary widely according to the type of catalyst used and the operating conditions.

It has now been found that the conversion and the selectivity can be considerably increased in the processes in which propylene or acrolein or the mixture of the two is oxidized catalytically in the vapor phase.

The present invention is based essentially on the discovery of the favourable effect of methanol on the values of the conversion and the selectivity in the catalytic oxidation of propylene and of acrolein.

The process of the present invention thus consists essentially in feeding small quantities of methanol together with propylene or acrolein or a mixture of the two into the reactor in which these substances are catalytically oxidized in the gaseous phase.

It is not convenient for methanol to be present in a quantity greater than 1% by volume with respect to the total gaseous mixture, either because one does not obtain appreciable advantages in the reaction yield in this case or because the catalysts for the oxidation of propylene and of acrolein are normally inhibited in the presence of methanol in quantities greater than that specified above.

On the other hand, it is not convenient for the methanol to fall to values below 0.01% by volume with respect to the total gaseous mixture, since appreciable advantages are not obtained in this case.

It should also be noted that the behaviour of methanol is unique, since other alcohols such as ethanol, when fed into the reactor in which propylene and acrolein are catalytically oxidized, do not in any way favour the conversion of the reactants and the selectivity for the desired products.

We do not know the mechanism of action of the methanol used in the process of the present invention.

In any case, while we do not wish ourselves to be bound in any way to some theory, we believe that methanol in the concentrations indicated appreciably inhibits the reactions that lead to the formation of by-products and equally favours those that lead to acrolein and acrylic acid.

The catalysts normally used in the preparation of acrolein by oxidation of propylene and of acrylic acid by oxidation of acrolein or of propylene or of mixtures of the two may be used as catalysts.

Thus the favourable influence of methanol on the conversion and selectivity of the processes described is smoothly exerted on the various combinations of cobalt, molybdenum, arsenic, tin, tellurium, manganese, nickel, bismuth, phosphorus, boron, iron, vanadium, rhenium, tungsten, zinc, or antimony, both as oxides and as compounds consisting of at least two of the metals mentioned and oxygen.

The catalysts, which are prepared by known methods, may be used by a fixed or moving or fluidized bed technique.

The methanol may be fed to the catalyst separately from the reactant gases or in a mixture with such gases.

The pressure is usually maintained at the atmospheric values, but the operation can also be carried out at up to 5 atm.

The temperature, on the other hand is maintained in the range from about 320° to 450°C, and preferably from about 350° to 420°C.

Under these conditions the best results are obtained by maintaining contact times in the reactor in the range from 0.1 to 6 seconds, and preferably from about 1 to 4 seconds.

The invention will now be illustrated by the following examples, which are not intended to limit it in any way.

EXAMPLE 1

For preparing a catalyst, 4.748 g of $Co(NO_3)_2 \cdot 6H_2O$ were dissolved in 50 ml of water in a beaker, and 4.316 g of ammonium heptamolybdate dissolved in 100 ml of water and 0.343 g of $(NH_4)_2HPO_4$ dissolved in 50 ml of water were then added.

The pH was adjusted to 8–9 by addition of an aqueous ammonia solution (concentration 32%), and 3 g of ammonium nitrate were then added.

After evaporation to dryness on a water bath followed by drying for 2 hours at 130°C, the activation of the residue was carried out.

For this purpose, the temperature was gradually raised at a rate of 50°C/hour to 400°C, and this value was maintained for 4 hours.

The catalyst prepared in this way was crushed and sieved to separate the fraction having diameters of from 50 to 200 microns.

3 ml of this fraction were charged into a steel reactor having an internal diameter of 12 mm.

Operating in a fixed bed at a temperature of 400°C and with a contact time of 2.5 seconds, a gaseous mixture consisting of 3.55% by volume of acrolein, 0.3% of methanol, and 10% of oxygen, the remainder consisting of nitrogen, was allowed to flow.

The reaction gas obtained had the following composition:
  0.55% of acrolein
  2.77% of acrylic acid
  0.63% of a mixture of CO and $CO_2$ A conversion of acrolein of 85% was obtained in this way with a selectivity (based on the reacted acrolein) for acrylic acid of 93.2%.

EXAMPLE 2

Using the same catalyst as in Example 1 and under the same operating conditions, but in the absence of methanol, a conversion of acrolein of 78% was obtained with a selectivity for acrylic acid of 80%.

EXAMPLE 3

For preparing a catalyst, 4.211 g of powdered metallic tellurium were dissolved at 60°C in 20 ml of 65% nitric acid.

17.656 g of $(NH_4)_6Mo_7O_{24} \cdot 4H_2O$ dissolved in 100 ml of $H_2O$ were added to the solution obtained in this way; 29.081 g of $Ni(NO_3)_2 \cdot 6H_2O$ and 2.00 g of ammonium nitrate dissolved in 100 ml of $H_2O$ were then added to the product obtained.

After evaporation to dryness on a water bath, the activation of the residue was carried out.

For this purpose, the temperature was first brought to 240°C and maintained at this value for 2 hours, then to 420°C and maintained at this value for 1 hour.

The catalyst prepared in this way was crushed and sieved to separate the fraction having diameters of from 100 to 200 microns.

3 ml of this fraction were charged into a steel reactor having an internal diameter of 12 mm.

Operating in a fixed bed at a temperature of 420°C and with a contact time of 4 seconds, a gaseous mixture consisting of 8% by volume of propylene and 0.1% of methanol, the remainder consisting of air, was allowed to flow.

A conversion of propylene of 90.5% was obtained with a selectivity (based on the reacted propylene) of 46.5% for acrolein and 24.6% for acrylic acid.

EXAMPLE 4

Using the same catalyst as in Example 3 and under the same operating conditions, but in the absence of methanol, a conversion of propylene of 85.7% was obtained with a selectivity (based on the reacted propylene) of 46.1% for acrolein and 22.2% for acrylic acid.

EXAMPLE 5

3 ml of the 50 to 200 micron fraction of a catalyst prepared as in Example 3 were charged into a steel reactor having an internal diameter of 12 mm.

Operating in a fixed bet at a temperature of 390°C and with a contact time of 3.5 seconds, a gaseous mixture consisting of 3% of propylene, 2.5% of acrolein, and 0.1% of methanol, the remainder consisting of air, was allowed to flow. The reaction gas obtained had the following composition:

0.7% of propylene
2.5% of acrolein
3.7% of acrylic acid
8.1% of $CO_2$
2.7% of CO A conversion of propylene of 91.2% was obtained in this way with a selectivity (based on the reacted propylene) for acrylic acid of 50.5%.

EXAMPLE 6

Using the same catalyst as in Example 5 and under the same operating conditions, but in the absence of methanol, a conversion of propylene of 87.3% was obtained with a selectivity (based on the reacted propylene) for acrylic acid of 47.8%.

EXAMPLE 7

1.276 g of powdered metallic tellurium were dissolved in 20 ml of 86% nitric acid.

The solution was evaporated to dryness, the product obtained was taken up in 50 ml of water, and the pH of the solution was adjusted to 8 by addition of 32 wt.% $NH_4OH$.

5.297 g of $(NH_4)_6Mo_7O_{24} \cdot 4H_2O$ dissolved in 100 ml of $H_2O$ were then added to the solution. Finally, 5.821 g of $Co(NO_3)_2 \cdot 6H_2O$ dissolved in 80 ml of $H_2O$ were also added.

After evaporation to dryness on a water bath followed by drying for 2 hours at 130°C, the activation of the residue was carried out.

For this purpose, the temperature was gradually raised at a rate of 50°C/hour to 400°C, and this value was maintained for 4 hours.

The catalyst prepared in this way was crushed and sieved to separate the fraction having diameters from 100 to 200 microns.

3 ml of this fraction were charged into a steel reactor having an internal diameter of 12 mm.

Operating in a fixed bed at a temperature of 400°C with a contact time of 2.5 seconds, a gaseous mixture consisting of 8.5% of propilene and 0.1% of methanol, the remainder consisting of air, was allowed to flow.

A conversion of propylene of 68.6% was obtained with a selectivity (based on the reacted propylene) for acrolein of 41.3%.

EXAMPLE 8

Using the same catalyst as in Example 7 and under the same operating conditions, but in the absence of methanol, a conversion of propylene of 65.3% was obtained with a selectivity (based on the reacted propylene) for acrolein of 36.8%.

What we claim is:

1. A process for the production of acrolein from propylene and acrylic acid from propylene or from acrolein or from mixtures of propylene and acrolein by reacting a gaseous mixture containing the said reactants and oxygen or a gas containing molecular oxygen in the presence of an oxidation catalyst consisting of combinations of cobalt, molybdenum, arsenic, tin, tellurium, manganese, nickel, bismith, phosphorus, boron, iron, vanadium, rhenium, tungsten, zinc, and antimony, either as oxides or as compounds consisting of at least two of the metals mentioned and oxygen, characterized in that the said gaseous mixture contains methanol in a quantity of from 0.01 to 1% by volume with respect to the total gaseous mixture.

2. Process as recited in claim 1, characterized in that the operation is carried out at a temperature in the range of from about 320° to 450°C, at a pressure in the range of from about 1 to 5 atm, and with a contact time in the range of from 0.1 to 6 seconds.

3. Process as recited in claim 2, characterized in that the operation is carried out at a temperature in the range of from about 350° to 420°C.

4. Process as recited in claim 2, characterized in that the operation is carried out with the pressure maintained at atmospheric values.

5. Process as recited in claim 2, characterized in that the operation is carried out at a temperature in the range of from about 350° to 420°C and with the pressure maintained at atmospheric values.

6. Process as recited in claim 2, characterized in that the operation is carried out with a contact time in the range of from about 1 to 4 seconds.

7. Process as recited in claim 6, characterized in that the operation is carried out at a temperature in the range of from about 350° to 420°C.

8. Process as recited in claim 6, characterized in that the operation is carried out with the pressure maintained at atmospheric values.

* * * * *